(12) United States Patent
Ringeisen et al.

(10) Patent No.: US 10,167,464 B2
(45) Date of Patent: Jan. 1, 2019

(54) CELL AND BIOFACTOR PRINTABLE BIOPAPERS

(71) Applicants: Bradley R. Ringeisen, Lorton, VA (US); Russell Kirk Pirlo, Washington, DC (US); Peter K. Wu, Ashland, OR (US)

(72) Inventors: Bradley R. Ringeisen, Lorton, VA (US); Russell Kirk Pirlo, Washington, DC (US); Peter K. Wu, Ashland, OR (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 279 days.

(21) Appl. No.: 14/177,240

(22) Filed: Feb. 11, 2014

(65) Prior Publication Data

US 2014/0154771 A1    Jun. 5, 2014

Related U.S. Application Data

(62) Division of application No. 13/097,124, filed on Apr. 29, 2011, now Pat. No. 8,669,086.

(60) Provisional application No. 61/329,525, filed on Apr. 29, 2010.

(51) Int. Cl.
*C12N 11/02*    (2006.01)
*C12N 5/00*     (2006.01)
*C12N 11/08*    (2006.01)
*C09D 7/63*     (2018.01)

(52) U.S. Cl.
CPC .............. *C12N 11/02* (2013.01); *C09D 7/63* (2018.01); *C12N 5/0068* (2013.01); *C12N 11/08* (2013.01); *C12N 2533/40* (2013.01); *Y10T 29/49826* (2015.01); *Y10T 428/24273* (2015.01)

(58) Field of Classification Search
USPC ......................................................... 435/177
See application file for complete search history.

(56) References Cited

U.S. PATENT DOCUMENTS

| 6,245,345 | B1* | 6/2001 | Swanbom | C08J 5/18 424/402 |
| 6,514,286 | B1* | 2/2003 | Leatherbury | A61L 27/12 623/11.11 |
| 2006/0036311 | A1* | 2/2006 | Nakayama | A61F 2/90 623/1.15 |
| 2007/0061015 | A1* | 3/2007 | Jensen | A61L 27/44 623/23.51 |
| 2009/0208577 | A1* | 8/2009 | Xu | A61L 27/38 424/484 |

OTHER PUBLICATIONS

Xu, Tao et al. Inkjet printing of viable mammalian cells. El sevier. Biomaterials 26 (2005) 93-99.*

* cited by examiner

*Primary Examiner* — Julie Wu
*Assistant Examiner* — Nghi V Nguyen
(74) *Attorney, Agent, or Firm* — US Naval Research Laboratory; Joseph T. Grunkemeyer

(57) ABSTRACT

Disclosed herein is a structure having: a porous polymeric film permeated by a first extracellular matrix material; and a topcoat layer comprising a second extracellular matrix gel disposed on the film. Also disclosed herein is a method of: providing a porous polymeric film; permeating the film with a first extracellular matrix material; and applying a topcoat layer of a second extracellular matrix material to the film. Also disclosed herein is a method of: laser-machining holes through a film comprising collagen to form a web-like structure.

9 Claims, 9 Drawing Sheets

CELL AND BIOFACTOR PRINTABLE BIOPAPERS

This application is a divisional application of allowed U.S. patent application Ser. No. 13/097,124 filed on Apr. 29, 2011, which claims the benefit of U.S. Provisional Application No. 61/329,525, filed on Apr. 29, 2010. The prior applications and all other publications and patent documents referred to throughout this nonprovisional application are incorporated herein by reference.

TECHNICAL FIELD

The present disclosure is generally related to tissue engineering

DESCRIPTION OF RELATED ART

Engineered tissues and organs have become a common goal in biomedical research. Engineered tissues and organs have the potential to provide replacements for diseased or damaged organs, solving the shortage of donor organs. Furthermore, with improved stem cell technologies, such engineered tissues could overcome the rejection problems associated with transplants. Additionally, engineered tissues may be useful for production of bioproducts and in hybrid devices such as sensors, computers, and machines.

Most all applications of tissue engineering, especially tissue and organ replacement, demand survival of heterogeneous cell structures in three-dimensions (3D). The organized 3D cell arrangement of an engineered tissue is required to promote the form and function of native tissue as well as to produce clinically relevant volumes of tissue.

The prevailing problem with engineering 3D tissues of increasing thickness is the limited transport of nutrients and waste. Without a compensatory transport technique such as flow reactors, or oxygen releasing polymers, cell proliferation and survival is constrained by the diffusion limits of oxygen to the outer 200 µm of the 3D tissue construct. This corresponds with the maximum tissue depth served by a capillary in native tissues.

There are many compelling reasons for addressing the problem of nutrient transport in 3D tissue constructs with a biological micro/vascular network: the self-mapping nature of angiogenesis to nutrient deficient areas of tissue, the reliance of many tissues development and function on the microvascular/cellular interaction (kidney, liver, pancreas) and accelerated anastomosis with native vasculature upon implantation. For these reasons, the dominant approach to nutrient transport limitations in 3D tissue constructs has become pre-vascularization.

There is a large body of research investigating how vascular and microvascular endothelial cells and their precursors develop into networks of lumens (tubulogenesis, vasculogenesis) when randomly seeded in hydrogel. While these studies offer insight into the mechanisms and conditions that influence vasculogenesis and angiogenesis, random seeding gives rise to an isotropic network of uniformly sized vessels. However, networks of blood vessels and capillaries in native tissues have an anisotropic self similar structure with size scaling which facilitates a directional flow of blood and transport of nutrients and waste.

Creation of 3D cultures, be they randomly seeded or patterned, almost always employ some type of solid scaffold, hydrogel, or combination scaffold. Poly(DL-lactide-co-glycolide) (PLGA) scaffolds are a popular choice because they degrade in a cell culture environment and leave behind no toxic agents. PLGA can be used as a scaffold material in rapid prototyping (pressure-assisted microsyringe (PAM)), micro-molding, foaming, or porogen leaching/solvent casting. To improve their biocompatibility and cell adhesion, PLGA scaffolds are often coated with collagen or filled with other extracellular matrix (ECM)-like hydrogels. ECM components have been shown to induce microvascular network formation. The positive effects of collagen on many cell types have lead to its use both as a primary scaffold material and as a membrane. With or without a solid scaffold material, the matrix density of ECM or hydrogels is influential on vasculogenesis.

The use of hydrogel scaffolds is integral to most 3D cell printing (sometimes referred to as organ printing) processes. 3D cell printing techniques like extrusion pens and inkjet printers are usually used to deposit both the hydrogel and the cells (either simultaneously or serially). There are two limitations to printing both the scaffolding and the cells together. First, the solvent used for the scaffold material must be non-toxic to cells (water-based). The vast majority of scaffolding materials printed by extrusion and ink jet cell printing approaches have therefore been hydrogels with very few examples using biodegradable polymer materials. Secondly, in order to limit clogging of the print-head (orifice) by the scaffolding material, the resolution of these techniques is limited to 100's µm.

BRIEF SUMMARY

Disclosed herein is a structure comprising: a porous polymeric film permeated by a first extracellular matrix material; and a topcoat layer comprising a second extracellular matrix gel disposed on the film.

Also disclosed herein is a method comprising: providing a porous polymeric film; permeating the film with a first extracellular matrix material; and applying a topcoat layer comprising a second extracellular matrix material to the film.

Also disclosed herein is a method comprising: laser-machining holes through a film comprising collagen to form a web-like structure.

BRIEF DESCRIPTION OF THE DRAWINGS

A more complete appreciation of the invention will be readily obtained by reference to the following Description of the Example Embodiments and the accompanying drawings.

FIG. 6 shows examples of the polymer film: 6(a) shows a hexagonal arrangement of uniform holes and 6(b) shows a web-like structure.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Though there are many hurdles to creating engineered tissues and organs, two of the challenges are 1) sustaining the health and development of three-dimensional tissues, especially over 1000 μm in thickness, via a vascular system; and 2) spatial patterning of heterogeneous tissues such as liver, kidney or brain tissues, or technically, any tissue type infiltrated by a vascular system containing vascular cells besides the primary tissue cell type.

Disclosed herein is an approach to creating 3D tissues. The method uses thin polymer scaffolds (biopapers) as a mechanically stable sheets to be used in a cell printing apparatus. Each polymer sheet can be addressed with different growth factors and then loaded into a cell printer for patterned cell seeding. After printing, each sheet can be cultured to achieve the desired level of cell differentiation (e.g., vasculature formation) and/or tissue formation and then stacked into three dimensional structures. By printing multiple cell types in a defined pattern to each sheet, culturing, and then stacking the sheets, these biopapers can be used to enable heterogeneous tissue structures to be created in 3D. By printing vascular and microvascular cell types in defined network structures, the structure, size, and direction of 3D vasculature can be influenced in a way that allows for flow of oxygen, nutrients, and waste into and out of the tissue. This is in contrast to the wealth of work where microvasculature networks are seeded randomly in a 3D block matrix or scaffold, creating a random, non-flow appropriate network. Often this 3D scaffold "block" technique results in a dead zone in the center of the scaffold as there is no pre-existing vascular network to carry nutrients in or waste out. The stacked biopaper method allows vasculature to be built into each level of a 3D (stacked) scaffold. This approach can work without surface patterned chemical cues, or mechanical restrictions, so it also allows for spontaneous formation of the smallest microvasculature structures, and takes advantage of the natural developmental processes arising from cell-cell and cell-matrix interactions. Printable, stackable biopapers may enable the creation of thick, spatially patterned, vascularized 3D tissues and potentially organs.

The biopapers are designed to 1) be used as a substrate for 2D cell printing; 2) enable handling and stacking to create a layered 3D construct; and 3) support the development of HUVEC networks while retaining fidelity of the printed pattern. Using a mold and a solvent casting/porogen leaching process, 200 μm×1 cm×1 cm biocompatible PLGA scaffold sheets were created. Depending on whether cell infiltration or network formation was desired, the scaffold sheets could be impregnated with an ECM substance, Collagen Type I or Matrigel, respectively. In order to produce HUVEC networks which retained the printed structure, the surface gel thickness was increased to 30 μm so as to decrease the mechanical influence of the relatively rigid PLGA scaffold on cell stretching. Four layer stacks of randomly seeded biopapers showed signs of interlayer merging and the feasibility for using these biopapers for layer-by-layer construction of 3D scaffolds. Biopaper substrates can be loaded with tissue specific hydrogels to support the desired cell type (here HUVEC). Biopapers enable the 2D cell printing techniques to be used to produce heterogeneously ordered 3D tissue constructs.

The disclosed materials and methods may enable 2D printing techniques to be used to create three-dimensional biological tissue constructs comprised of multiple cell types with defined spatial arrangements.

Stacking rigid scaffold sheets is an alternative to layering hydrogels and can be used to introduce polymer scaffolds without cytotoxic solvents. Described herein is the fabrication of thin polymer scaffold sheets (biopapers) for use in cell printing applications. Various biopapers have been made and used in a cell printer using biological laser printing (BioLP™) (U.S. Pat. Nos. 7,294,367 and 7,381,440). Biopapers were patterned with high resolution (<30 μm) 2D cell printing and then stacked to enable thick 3D tissue constructs to be created with well defined 3D cell arrangements. Besides mimicking the cell-cell arrangements of native tissue types, this approach could be particularly useful in prevascularization of engineered thick tissues. By stacking 200 μm sheets prepared in this way, it may be possible to create anisotropic vascular networks with a spacing which resembles that of native tissue and mimics the structure/pattern of angiogenesis in the mammalian circulatory system. Towards this end cell printing onto hybrid "biopapers" that contain bilayers of PLGA and extracellular matrix (ECM) has been performed. Not only are these biopapers compatible with cell printing for forming patterns of cells, they also are stackable to form 3D cell constructs and support the formation of vascular networks.

The polymeric film provides structural support for the biopaper during handling. The choice of polymer may depend upon the types of cells to be placed on it. Suitable polymers include, but are not limited to, poly(DL-lactide-co-glycolide) (PLGA) and collagen. PLGA is somewhat stiffer than collagen, such that collagen may be preferred for neural or brain cells.

The polymer film is porous and may or may not be a non-woven material. The porous may be may be any means for creating empty regions in the film. The pores may be smaller than the thickness of the film or may be holes that traverse the entire thickness of the film. Suitable methods of forming the pores include, but are not limited to particulate leaching, solvent casting, and micromolding.

Figure 6A:
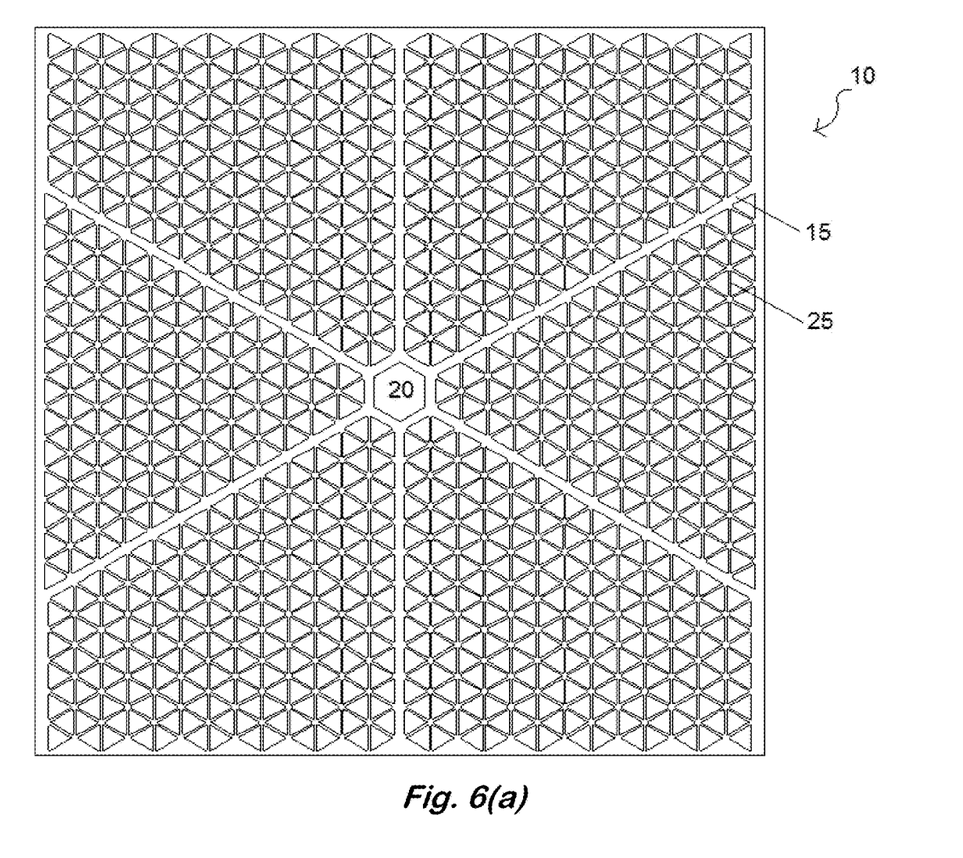
Figure 6B:
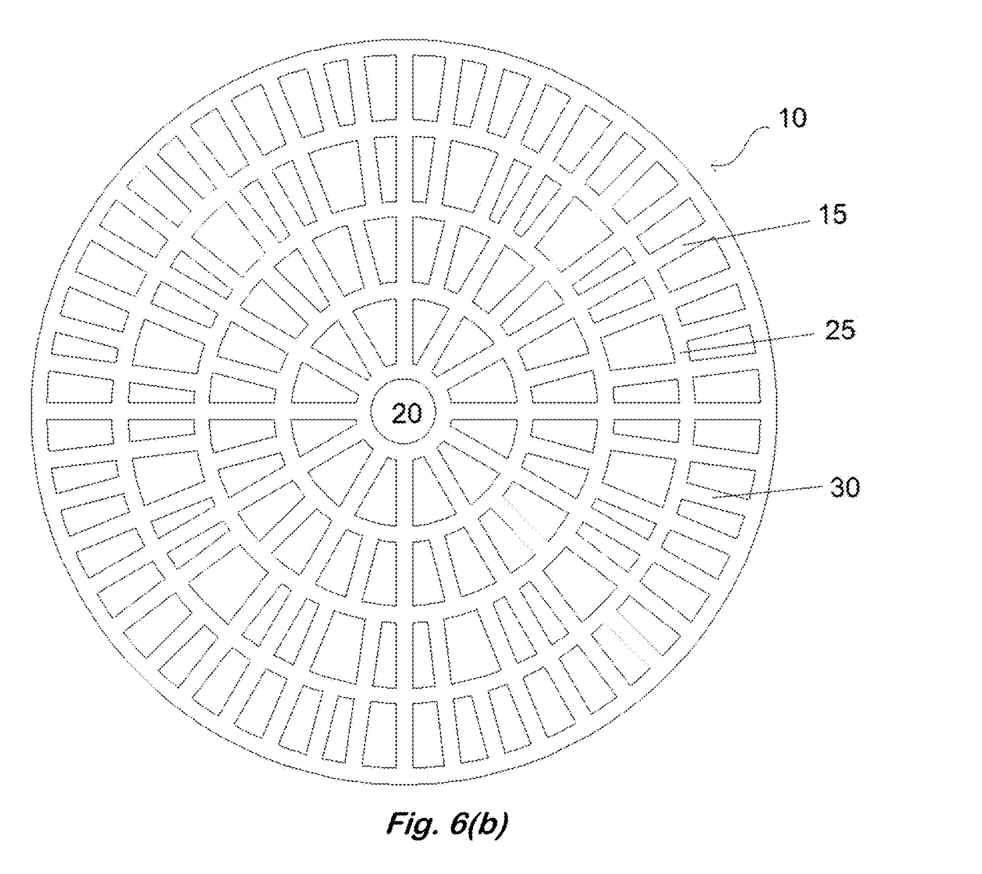

Another method of forming the pores is by creating holes through the film by laser machining, collagenase digestion, molding, or other means. One possible configuration of the holes is a hexagonal arrangement of uniform holes. The holes may also be placed to form a web-like structure in the remaining film. Two web-like structures 10 are exemplified in FIG. 6. A web-like structure is defined herein as comprising a plurality of elongated radial members 15 radiating from a central region 20 and a plurality of first order crossing members 25 that are connected to adjacent radial members 15. Optionally, the structure may include second order crossing members 30 connected to adjacent first order crossing members 25, third order crossing members (not shown) connected to adjacent second order crossing members 30, etc. The crossing members may connect all possible pairings of adjacent members that they connect to, and may cross each other as in FIG. 6(b). The holes between the members may be small enough to support the extracellular matrix. The spacing between members may be, for example, 100-200 μm. The film may be, for example, up to 30-50 μm thick, and may be made from dry collagen such as that used to make a sausage casing.

The first and second extracellular matrix may be the same or different materials, and may be in the form of a gel or hydrogel. Suitable material include, but are limited to, collagen, laminin, a mixture of collagen and laminin, hyaluronic acid, and any mixture thereof. Hydroxyapatite is also a suitable matrix for the topcoat for growth of bone cells. The matrix may optionally comprise biologically useful materials, including but not limited to a growth factor, a differentiation-inducing factor, an anti-apoptotic factor, a bio-active factor, or a synthetic peptide sequence. Matrigel® is a commercially available material that includes collagen, laminin, and some of the factors named above. A given material may be used in different forms for different components of the structure. For example, a dry collagen film may be permeated and topcoated with a wet collagen gel or hydrogel.

Figure 8:
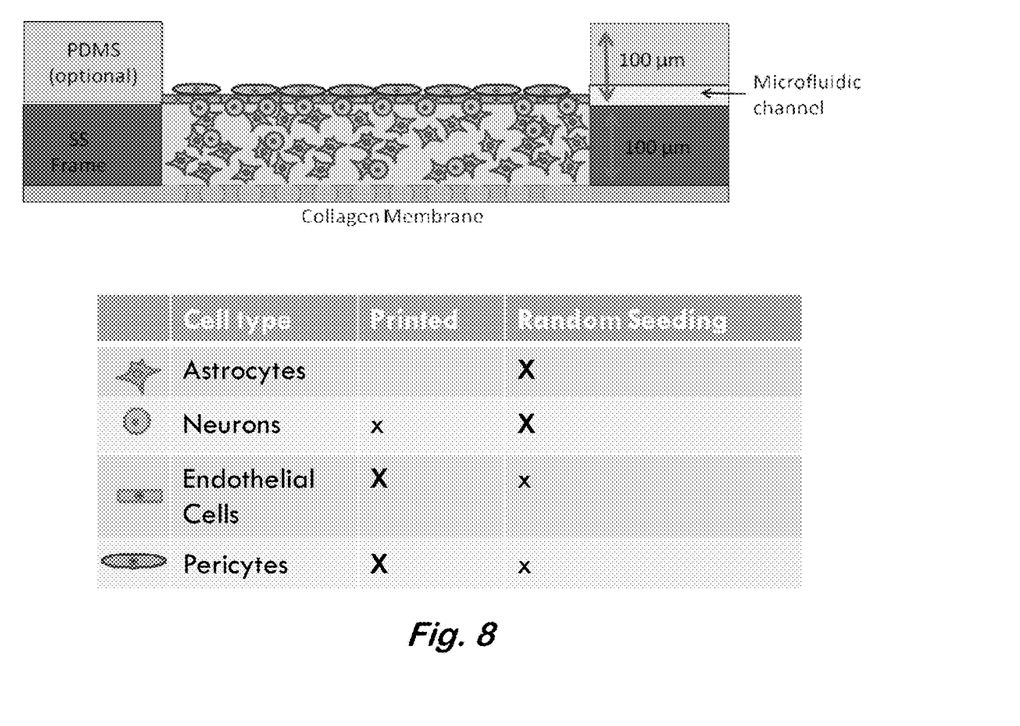
FIG. 8 schematically illustrates a frame used with a collagen membrane and various neural cells.

The total thickness of the structure is may make it suitable for handling during the application of cells to the structure without damage. The total thickness may be, for example, 50-500 μm or 100-300 μm. This thickness is divided between the film and the topcoat. When necessary from structural integrity, the film may compose a majority of the thickness with a thin top coat. A thinner film may be used when the film is placed within or on a rigid holding frame. Such a frame may comprise, for example, a metal such as aluminum for permanence, or a degradable polymer such as PLGAS when the frame will ultimately not be needed anymore. The frame may also comprise a non-degradable elastic polymer and/or have a microfluidic interface to the film. The interface can allow for the flow if nutrients and waste to and from the film. FIG. 8 schematically illustrates a frame used with a collagen membrane and various neural cells.

The structure may comprise a plurality of living cells disposed on or within the topcoat layer to form a cell-seeded structure. These cells may include the cells originally placed on the structure and/or new cells grown or differentiated from the original cells. Any method of placing the cells that allows for at least some viable cells on the structure may be used. Suitable methods include, but are not limited to, a laser transfer method, laser-based printing, ink jet printing, micropen printing, syringe deposition, electrospray deposition, and a conformal printing method. One suitable laser method is BioLP™, described in U.S. Pat. Nos. 7,294,367; 7,381,440; and 7,875,324. Other methods that may be applicable to the presently disclosed methods are described in Ringeisen et al., "Jet-based methods to print living cells", *Biotechnol. J.* 1, 930-948 (2006); Ringeisen et al., *Biomaterials* 23, 161-166 (2002); Ringeisen et al., *Tissue Eng* 10 (3-4): 483-491 (2004); Chen et al., *App. Surf. Sci.* 252, 8641-8645 (2006); Barron et al., *Annals of Biomed Engineering,* 33 (2): 121-130 (2005); Wu et al., "BioLP Printing and Development of HUVEC and HUVSMC Branch/Stem Structure on Hydrogel Layers", *Biofabrication* 2 (2010) 014111; and U.S. Pat. Nos. 6,177,151; 6,805,918; 6,815,015; 6,905,738; and 6,936,311.

The cells may be placed in random or random-like arrangements, in an anisotropic arrangement, or both. Anisotropic arrangement may be useful for vascular cells to enable the formation of a vascular network throughout the structure. Any other type of cell may be used including, but not limited to, neural cells, endothelial cells, osteoblasts, neurons, astrocytes, and hepatocytes. Any cells capable of growth and/or differentiation may also be used.

Figure 7:
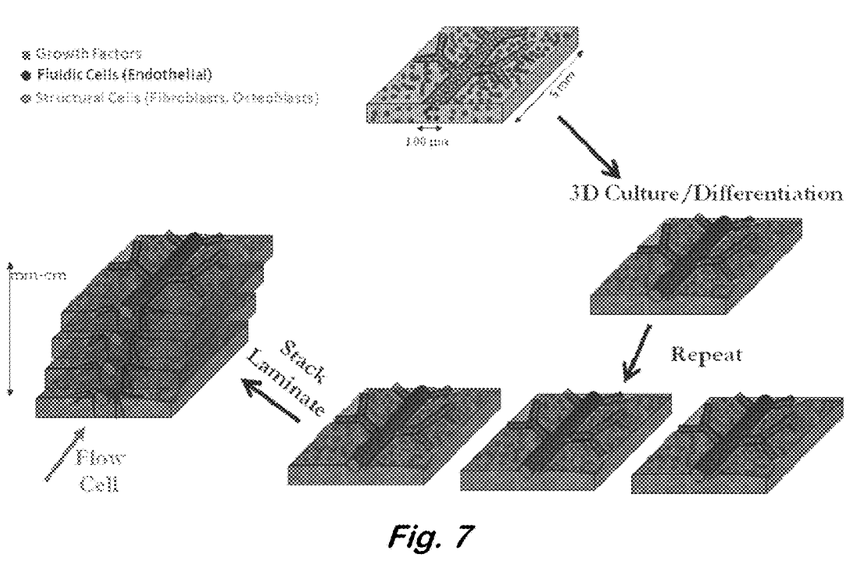
FIG. 7 schematically illustrates the printing and stacking process.

A plurality of the structures with cells may be stacked to form a stacked structure having alternating layers of polymeric film and topcoat layers. The stacked structure may be incubated under conditions to induce cell differentiation or cell growth, including the use of growth factors. This method may be used to form a three-dimensional tissue. Incubation may also occur in individual layers that may be stacked afterward. FIG. 7 schematically illustrates the printing and stacking process. Such a structure may be useful as a brain tissue simulant for testing ballistic damage.

The following examples are given to illustrate specific applications. These specific examples are not intended to limit the scope of the disclosure in this application.

Example 1 (Comparative)

Polymer Film without a Topcoat—

Biopaper sheets were fabricated using a solvent casting/particulate leaching method with 3.6% w/v Poly(DL-lactide-co-glycolide) $M_w$ 40,000-75,000, lactide:glycolide (65:35) Lactel® (Sigma #BP-0200) in chloroform with pores formed by +80 MESH (177 μm) NaCl powder (GFS Chemicals, Inc.). The PLGA scaffolds were cast in rectangular molds formed by 1 mm thick polydimethylsiloxane (PDMS) placed on glass. The NaCl porogen was leached with at least 6 serial rinses in DI water for 1 hour each. Once rinsed the air dried over night the PDMS mold was peeled away from the glass leaving the PLGA scaffold strips on the glass. A sharp razor blade was used to separate the scaffold strips from the glass and they were rinsed once more. After drying again the strips of scaffold were cut into 1×1 $cm^2$ squares. Two days prior to use, the PLGA squares were covered with a stainless steel mesh and submerged in basal medium under a vacuum to pre-wet them and remove air bubbles.

For 3D cell culture experiments, Collagen Type I from rat tail (BD Biosciences 3.67 mg/mL) was brought to alkalinity with 1M NaOH and mixed with an equal amount of cell suspension (5×$10^6$ cells/mL) yielding a collagen density of 1.835 mg/mL. Wetted scaffolds were removed from media and placed in a Petri dish. Excess medium was removed from the paper with a Pasture pipette placed on the dish bottom next to the papers edge. The paper was infused with cells and collagen by pipetting 50-100 μL of collagen/cell suspension onto the surface and any excess suspension which seeped out was gently removed with the micropipetter. The papers were then placed in the incubator for 45 min to allow the collagen to gel and cells to attach. After initial seeding, a sterile stainless steel mesh was placed over the biopaper and medium was added. Media was changed after 24 hours and then every 2 days.

Example 2

Polymer Film with a Topcoat—

Some experiments involved printing or randomly culturing human umbilical vein endothelial cells (HUVECs) on the surface of biopapers with the expectation of network formation. For these experiments, Matrigel® (BD Biosciences) was used as the ECM hydrogel. Unseeded scaffold sheets were removed from the wetting medium and placed onto 22 $mm^2$ glass coverslips in 35 mm Petri dishes and then cooled in a 4° C. refrigerator. Matrigel® was thawed and kept on ice. Petri dishes containing PLGA scaffolds were then placed on ice. Excess media was removed from the scaffolds with a Pasteur pipette and 50-100 μL Matrigel® was then micropipetted onto the scaffolds. The biopapers were then allowed to gel in a humidified incubator at 37° C.

for 1 hour. After being gelled these scaffolds were considered as biopapers without a topcoat. To create biopapers with a 30 μm topcoat, an additional 30 μL of Matrigel® was pipetted to the surface of the biopaper and placed back into the incubator to gel again. The 30 μm thickness was estimated by the volume of Matrigel® divided by the paper area and checked by measuring the Z distance between focus on pore surface and gel surface using confocal microscopy.

Figure 1:
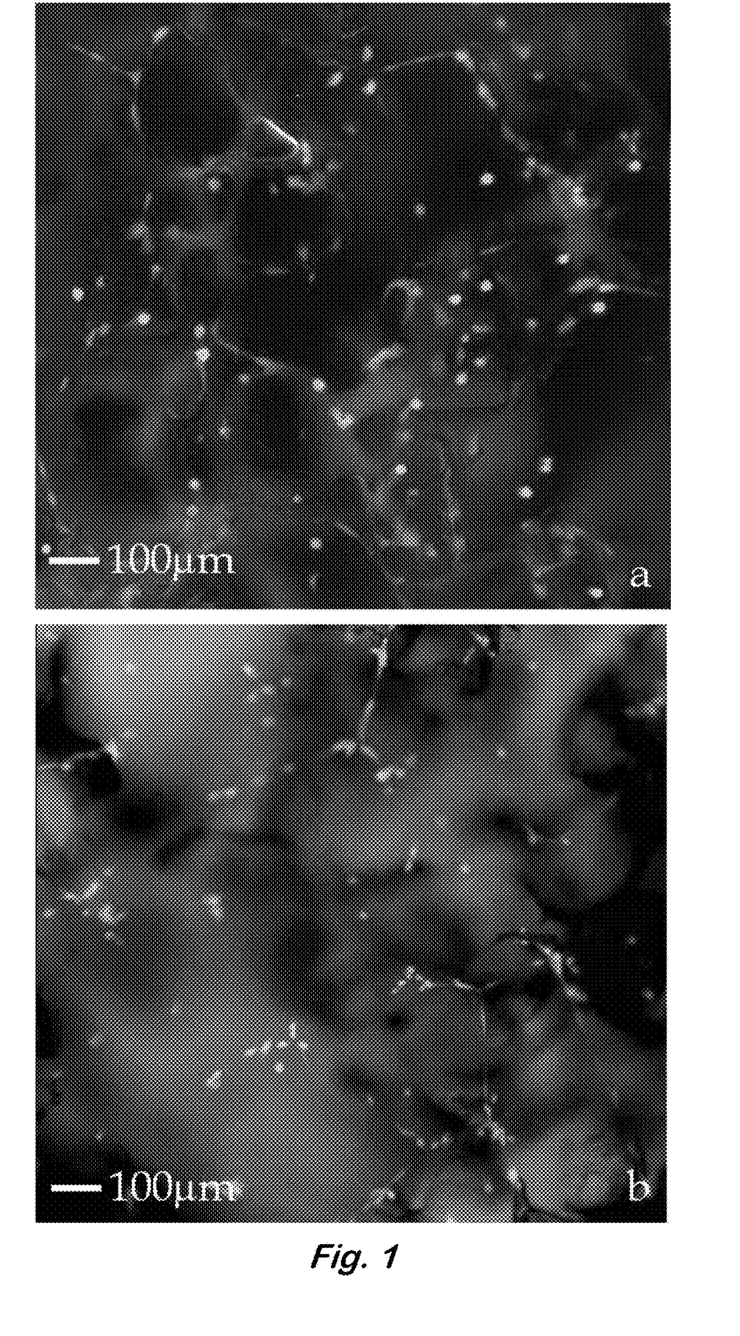
FIG. 1 shows (a) a fluorescent microscope image of live/dead stained HUVECs on a biopaper without topcoat and (b) the fluorescent live/dead image of the resulting HUVEC network on a thick Matrigel® top coat

Test 1: Ability of Paper to Support Cell Differentiation:

HUVECs were seeded on Matrigel®-loaded biopapers with and without an additional 30 μm top coat of Matrigel® to determine whether typical network morphology developed. FIG. 1(a) shows a fluorescent microscope image of live/dead stained HUVECs on a biopaper without topcoat. FIG. 1(b) shows the fluorescent live/dead image of the resulting HUVEC network on a thick Matrigel® top coat. The live/dead stain shows that nearly 100% of the seeded cells remain viable on biopapers with and without a Matrigel® topcoat after 24 hours of culture. However, there is a noticeable difference in the extent to which the HUVEC network morphology adheres to the PLGA pore morphology. Without the 30 μm topcoat, the HUVECs form networks along the rigid boundaries of the scaffold.

Figure 2:
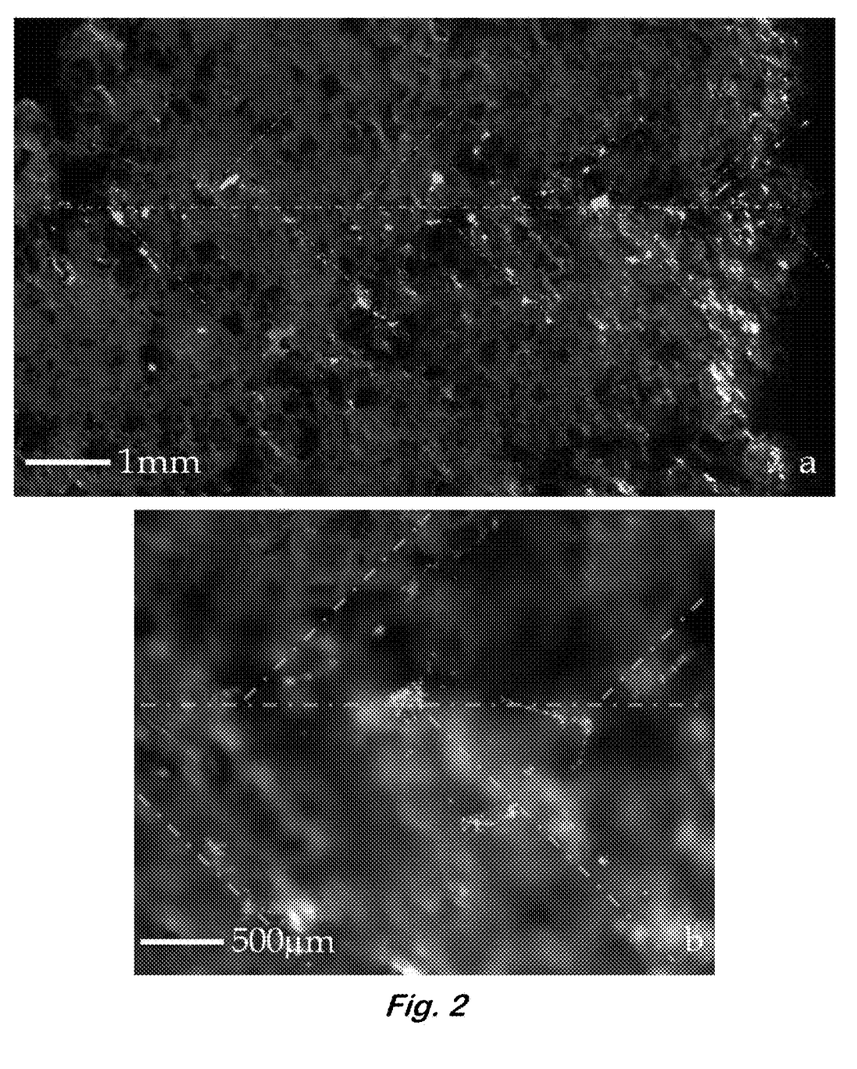
FIG. 2(a) shows HUVECs printed to a Matrigel® loaded biopaper in a stem and 45° branch pattern.
FIG. 2(b) is a higher magnification image.

Test 2: Ability of Paper to Support BioLP Printing and Retain Fidelity of Printed Cell Structures:

A typical result of HUVECs printed to a Matrigel® loaded biopaper in a stem and 45° branch pattern is shown in FIGS. 2(a) and (b). The live/dead stain indicates that greater than 95% of the printed cells are viable on the biopapers after 24 hours of culture. FIG. 2(b) is a higher magnification image of the printed HUVEC structure. Many of the printed HUVECs have begun linking along the length of the branched pattern (dashed line shows original stem/branch printed pattern).

Figure 3:
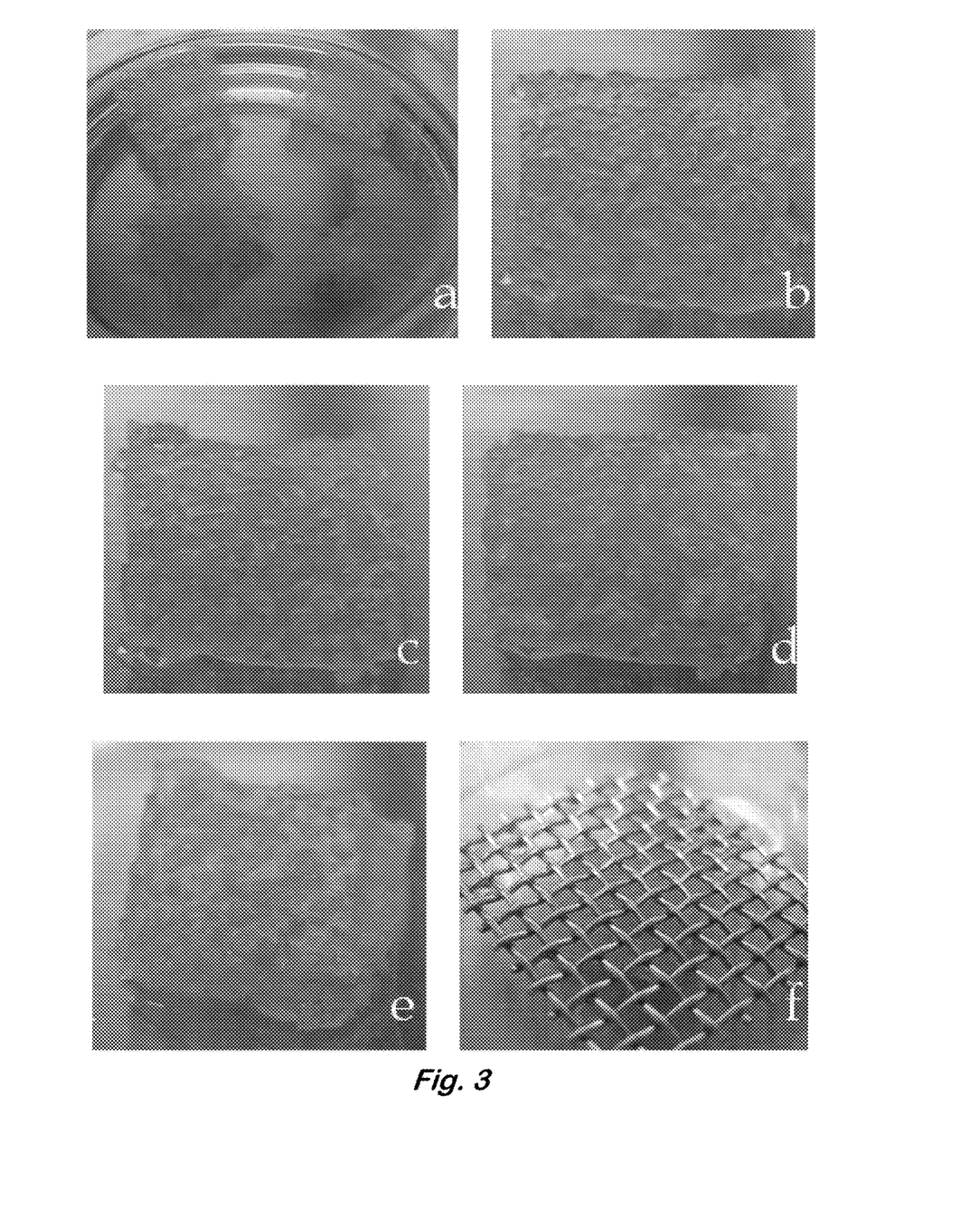
FIG. 3 shows optical photographs of seeded papers in culture (a), individually (b), and successively stacked (c-f).
Figure 4:
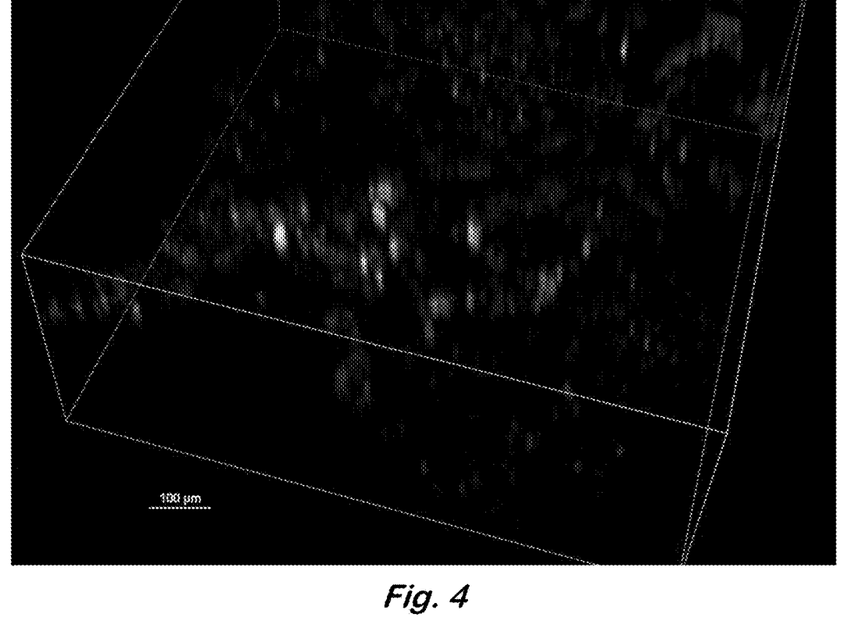
FIG. 4 shows the maximum intensity projection of a 3D confocal microscopy scan of a live/dead stained construct FIG. 5 clear through imaging of a stacked construct.
Figure 5:
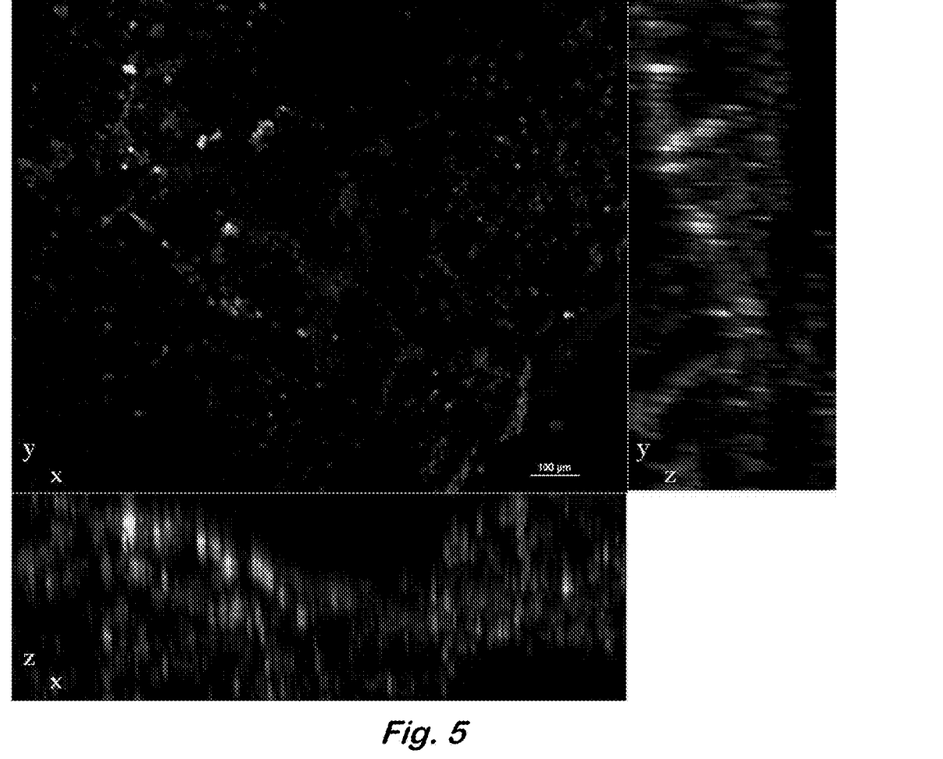

Test 3: Stack Ability of Papers, Interlayer Interaction:

Individual biopapers were randomly seeded throughout with HUVECs in collagen for 1 day prior to stacking. FIG. 3 shows optical photographs of the seeded papers in culture (a), individually (b), and successively stacked (c-f). The stacked construct was held down with a stainless steel mesh and cultured for 4 more days. FIG. 4 shows the maximum intensity projection of a 3D confocal microscopy scan of the live/dead stained construct. Because of the opacity and diffraction of the PLGA papers, clear through imaging of the stacked construct was performed at scattered sites in the XY plane of the biopaper where several pores were aligned to form a clear through hole or a nearly clear-through hole in the scaffolding (FIG. 5). After 5 days of culturing, the construct had compressed to a total thickness of about 400 μm. 3D confocal microscopy of stacked biopapers at 5 days showed a cell density of $1.3 \times 10^6$ cells/cm$^3$. Of these cells, live/dead staining showed a viability of less 25%.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
    providing a plurality of structures each comprising:
        a porous polymeric film having pores permeated by a first extracellular matrix material; and
        a topcoat layer comprising a second extracellular matrix gel disposed on the film;
    placing living cells on or within each topcoat layer to form cell-seeded structures; and
    stacking the cell-seeded structures to form a stacked structure having alternating layers of polymeric film and topcoat layers;
        wherein at least one of the cell-seeded structures has cells positioned in a branched pattern before the cell-seeded structures are stacked.

2. The method of claim 1, wherein the cells are placed by a laser transfer method, laser-based printing, ink jet printing, micropen printing, syringe deposition, electrospray deposition, or a conformal printing method.

3. The method of claim 1, further comprising:
    incubating the stacked structure under conditions to induce cell differentiation or cell growth.

4. The method of claim 3, wherein the first or second extracellular matrix material comprises a growth factor.

5. The method of claim 1, wherein the living cells are placed in the branched pattern.

6. The method of claim 1, wherein the living cells are placed in a branched pattern comprising more than one type of cell.

7. The method of claim 1, wherein providing the structure comprises:
    providing the porous polymeric film; and
    permeating the film with the first extracellular matrix material;
        wherein the film is not cell-seeded.

8. The method of claim 1, wherein the branched pattern is formed by incubating the cell-seeded structures before stacking.

9. The method of claim 1, wherein the stacked structure comprises a vascular network that allows for flow of materials into and out of the stacked structure.

* * * * *